United States Patent
Del Cid et al.

(10) Patent No.: US 11,696,798 B2
(45) Date of Patent: Jul. 11, 2023

(54) COATED ELECTROSURGICAL VESSEL SEALER ELECTRODES

(71) Applicant: CONMED CORPORATION, Utica, NY (US)

(72) Inventors: Roberto Del Cid, Denver, CO (US); Michael Lontine, Highlands Ranch, CO (US); Michael Olichney, Castle Rock, CO (US); Mason Williams, Centennial, CO (US)

(73) Assignee: CONMED CORPORATION, Utica, NY (US)

( * ) Notice: Subject to any disclaimer, the term of this patent is extended or adjusted under 35 U.S.C. 154(b) by 563 days.

(21) Appl. No.: 16/622,980

(22) PCT Filed: Jun. 15, 2018

(86) PCT No.: PCT/US2018/037697
§ 371 (c)(1),
(2) Date: Dec. 16, 2019

(87) PCT Pub. No.: WO2018/232206
PCT Pub. Date: Dec. 20, 2018

(65) Prior Publication Data
US 2021/0145507 A1 May 20, 2021

Related U.S. Application Data

(60) Provisional application No. 62/520,126, filed on Jun. 15, 2017.

(51) Int. Cl.
*A61B 18/14* (2006.01)
*A61B 17/00* (2006.01)
*A61B 18/00* (2006.01)

(52) U.S. Cl.
CPC ............... *A61B 18/1445* (2013.01); *A61B 2017/00526* (2013.01); *A61B 2018/0013* (2013.01);
(Continued)

(58) Field of Classification Search
CPC ...... A61B 18/1445; A61B 2017/00526; A61B 2018/00083; A61B 2018/0013;
(Continued)

(56) References Cited

U.S. PATENT DOCUMENTS 5,843,019 A * 12/1998 Eggers ............... A61M 25/0133
606/41
5,891,142 A * 4/1999 Eggers ............... A61B 18/1442
606/51

(Continued)

FOREIGN PATENT DOCUMENTS

EP 1259183 11/2002
EP 1905370 4/2008
(Continued)

OTHER PUBLICATIONS

KR Office Action dated Apr. 28, 2021, Application 10-2019-7038821, pp. 1-10.

*Primary Examiner* — Ronald Hupczey, Jr.
(74) *Attorney, Agent, or Firm* — Bond, Schoeneck & King, PLLC

(57) ABSTRACT

A vessel sealing device having a pair of electrodes that are maintained in spaced apart configuration when closed by non-uniform coating formed from a non-conductive material that has been applied to roughened electrodes so that the coating allows for the passage of a predetermined amount of radiofrequency (RF) energy between the electrodes. The coating has a predetermined thickness that spaces the electrodes apart while also having the predetermined non-uniformity that allows RF energy to pass between the
(Continued)

electrodes when a vessel is trapped therein, thus desiccating the vessel positioned in the jaws. The electrodes may include a series of grooves in a herringbone pattern, with each electrode having the pattern oriented in the same direction or in opposite directions.

8 Claims, 18 Drawing Sheets

(52) U.S. Cl.
  CPC ............... *A61B 2018/0063* (2013.01); *A61B 2018/00083* (2013.01); *A61B 2018/00386* (2013.01); *A61B 2018/00404* (2013.01)

(58) Field of Classification Search
  CPC ........... A61B 2018/00386; A61B 2018/00404; A61B 2018/0063; A61B 2018/00136; A61B 2018/1455; A61B 2090/034; A61B 2018/00345; B05D 3/0254; B05D 3/12; B05D 5/02; B05D 5/08
  See application file for complete search history.

(56) References Cited

U.S. PATENT DOCUMENTS

| | | | |
|---|---|---|---|
| 5,893,846 A | 4/1999 | Bales et al. | |
| 6,139,547 A * | 10/2000 | Lontine | A61B 18/1402 606/49 |
| 6,149,620 A * | 11/2000 | Baker | A61M 25/0133 604/22 |
| 6,264,650 B1 * | 7/2001 | Hovda | A61B 18/148 606/41 |
| 6,264,651 B1 * | 7/2001 | Underwood | A61B 18/1402 606/41 |
| 6,494,881 B1 * | 12/2002 | Bales | A61B 18/149 606/49 |
| 6,613,048 B2 * | 9/2003 | Mulier | A61B 18/1445 606/49 |
| 6,773,409 B2 * | 8/2004 | Truckai | A61B 18/1815 606/49 |
| 6,887,240 B1 * | 5/2005 | Lands | A61B 17/29 606/51 |
| 6,926,716 B2 | 8/2005 | Baker et al. | |
| 8,877,846 B2 | 11/2014 | Moorlag et al. | |
| 10,966,780 B2 | 4/2021 | Garrison | |
| 2001/0037110 A1 * | 11/2001 | Schmaltz | A61B 18/1445 606/50 |
| 2002/0062123 A1 * | 5/2002 | McClurken | A61B 18/1442 606/34 |
| 2002/0111624 A1 * | 8/2002 | Witt | A61B 18/1442 606/51 |
| 2003/0014053 A1 * | 1/2003 | Nguyen | A61B 18/1445 606/51 |
| 2003/0018331 A1 * | 1/2003 | Dycus | A61B 18/1445 606/51 |
| 2003/0069571 A1 * | 4/2003 | Treat | A61B 18/085 606/29 |
| 2003/0171748 A1 * | 9/2003 | Truckai | A61B 18/1442 606/51 |
| 2003/0181910 A1 * | 9/2003 | Dycus | A61B 18/1445 606/51 |
| 2003/0229344 A1 * | 12/2003 | Dycus | A61B 18/1445 606/51 |
| 2004/0006340 A1 * | 1/2004 | Latterell | A61B 18/1442 606/48 |
| 2004/0147922 A1 * | 7/2004 | Keppel | A61B 18/14 606/41 |
| 2005/0021026 A1 * | 1/2005 | Baily | A61B 18/1445 606/51 |
| 2005/0033278 A1 * | 2/2005 | McClurken | A61B 18/14 606/49 |
| 2006/0217697 A1 * | 9/2006 | Lau | A61B 18/085 606/29 |
| 2006/0217706 A1 * | 9/2006 | Lau | A61B 17/29 606/45 |
| 2007/0078456 A1 * | 4/2007 | Dumbauld | A61B 18/1445 606/42 |
| 2008/0077131 A1 * | 3/2008 | Yates | A61B 17/07207 606/51 |
| 2008/0188844 A1 * | 8/2008 | McGreevy | A61B 18/082 606/28 |
| 2008/0188845 A1 * | 8/2008 | McGreevy | A61B 18/085 606/29 |
| 2008/0234672 A1 * | 9/2008 | Bastian | A61B 18/1445 606/41 |
| 2010/0069904 A1 * | 3/2010 | Cunningham | A61B 18/14 606/48 |
| 2010/0076433 A1 * | 3/2010 | Taylor | A61B 18/1445 606/170 |
| 2010/0179545 A1 * | 7/2010 | Twomey | A61B 18/1445 606/51 |
| 2011/0184404 A1 * | 7/2011 | Walberg | A61B 18/1445 606/41 |
| 2013/0274736 A1 * | 10/2013 | Garrison | A61B 18/1445 606/41 |
| 2015/0272606 A1 * | 10/2015 | Nobis | A61B 18/1445 606/170 |
| 2015/0374430 A1 * | 12/2015 | Weiler | A61B 18/1445 606/46 |
| 2016/0022352 A1 * | 1/2016 | Johnson | A61B 18/14 606/41 |
| 2017/0119456 A1 * | 5/2017 | Sartor | A61B 18/1442 |
| 2018/0153613 A1 * | 6/2018 | Weisshaupt | A61B 18/1445 |
| 2018/0280075 A1 * | 10/2018 | Nott | A61B 18/1445 |

FOREIGN PATENT DOCUMENTS

| | | |
|---|---|---|
| JP | 2008-73531 | 12/2012 |
| KR | 10-2014-0063727 | 5/2014 |
| WO | 2016/184796 | 11/2016 |

* cited by examiner

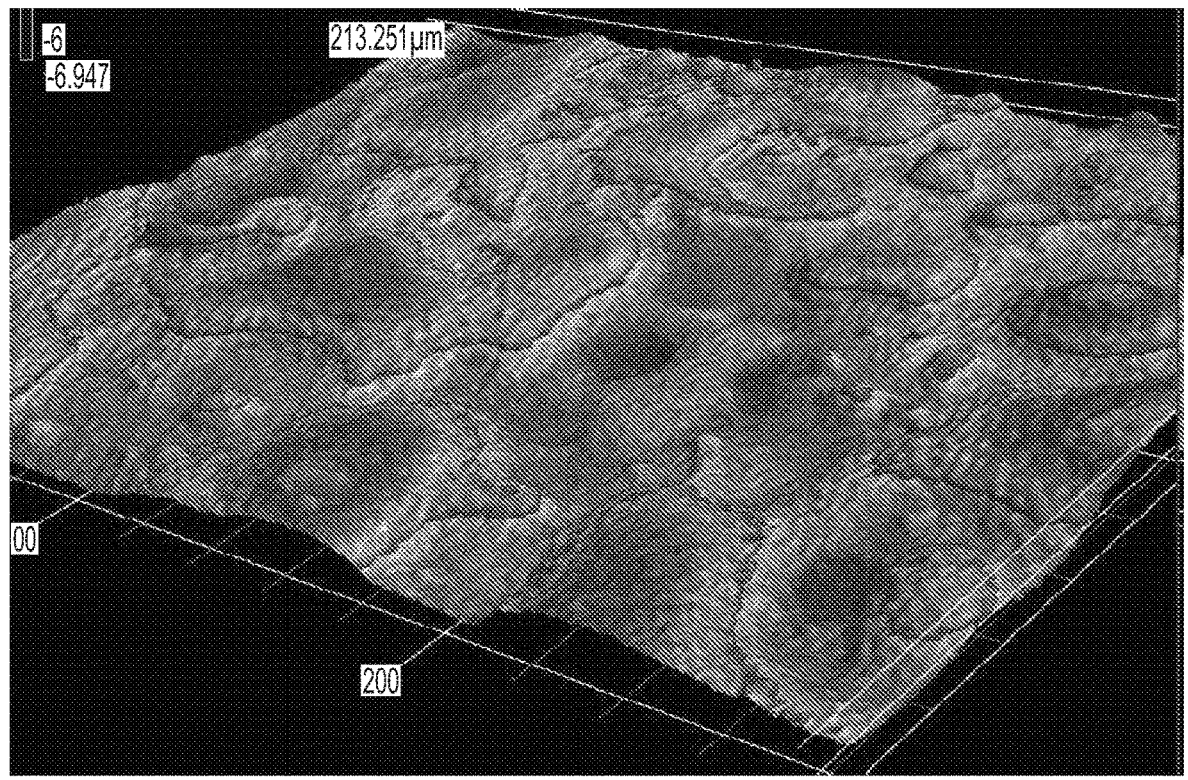
TOTAL PROFILE
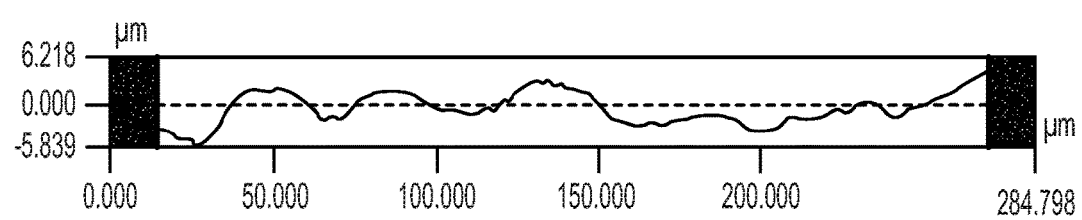
ROUGHNESS PROFILE
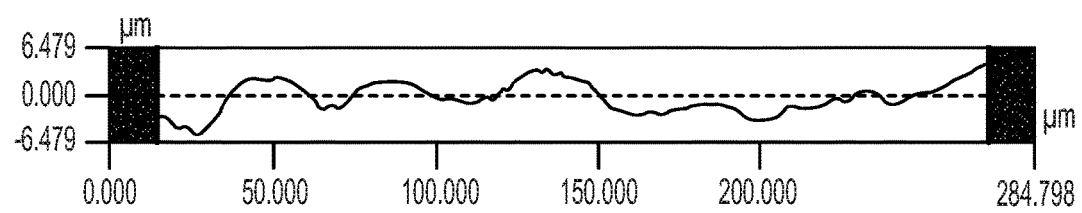
FIG. 18

COATED ELECTROSURGICAL VESSEL SEALER ELECTRODES

CROSS-REFERENCE TO RELATED APPLICATIONS

The present application claims priority to U.S. Provisional App. No. 62/520,126, filed on Jun. 15, 2017.

BACKGROUND OF THE INVENTION

1. Field of the Invention

The present invention relates to electrosurgical vessel sealers and, more specifically, vessel sealing electrodes that are coated with a non-conducting material to provide the requisite gap distance between the electrodes.

2. Description of the Related Art

Electrosurgical vessel sealers are used for the occlusion of blood vessels and halting of bleeding during surgical procedures. The electrodes of the vessel sealer are interconnected to an electrosurgical generator that can selective supply radiofrequency (RF) energy to the electrodes for the desiccation and sealing of a blood vessel that has been clamped between the electrodes. A blade may be additionally incorporated into the jaws for cutting of the sealed blood vessel along an intermediate portion of the seal created by the energized electrodes.

For safe and effective operation, the electrodes of the vessel sealer must remain separated by approximately 0.002 to 0.006 inches (0.0508 to 0.1524 millimeters) when clamping a blood vessel to prevent arcing or shorting when the electrodes are energized. As the blood vessel does not typically occupy the entire region between the electrodes, there is a constant risk that the electrodes will be allowed to come into contact with each other or become so closely positioned that arcing or shorting will occur. Current approaches for maintaining the appropriate electrode separate involve non-conducting blocks or stops that are positioned along the electrodes to physically prevent the electrodes from becoming too closely positioned relative to each other when energized. While stops can maintain the proper distance between the electrodes, they are difficult to install and thus increase the costs and complexity involved in the manufacturing of the vessel sealer. Accordingly, there is a need in the art for an approach that can ensure the appropriate gap between the electrodes of the vessel sealer without the need to form or place physical stops along the jaws.

BRIEF SUMMARY OF THE INVENTION

The present invention is a vessel sealing device that uses a non-conductive coating that is applied non-uniformly to the electrodes of the device to maintain adequate separation of the electrodes while allowing sufficient RF energy to pass between the electrodes to seal any vessel positioned therebetween. The vessel sealing device comprises a pair of electrodes that are moveable between open and closed positions and a coating formed from a non-conductive material applied non-uniformly to at least one of the pair of electrodes such that radiofrequency (RF) energy will only pass between the pair of electrodes if a vessel is positioned therebetween in contact with the pair of electrodes. The coating may be applied non-uniformly to both of the pair of opposing electrodes. The coating may be applied non-uniformly such that the coating on each of the pair of electrodes has a total profile that varies between −5.8 micrometers and 6.2 micrometers from a centerline average. The coating may be applied non-uniformly such that the coating on each of the pair of electrodes has a roughness profile that varies between −6.5 micrometers and 6.5 micrometers from a centerline average. The vessel sealing device may further comprise a series of grooves formed in the face of each of the opposing electrodes. The coating may vary in thickness between the face and the grooves formed in the face. The series of grooves of the face of each of the opposing electrodes may extend transversely to the longitudinal axis of the face of each of the opposing electrodes. The series of grooves of the face of each of the opposing electrodes may be oriented in a herringbone pattern. The face of each of the opposing electrodes may extend from two opposing side walls to an inner track. The coating may further extend across at least a portion of the side walls.

A method of making a vessel sealing device having a pair of opposing electrodes according to the present invention comprises texturing the face of at least one of the opposing electrodes and applying a non-conductive material non-uniformly to the textured face such that RF energy will only pass between the pair of electrodes if a vessel is positioned therebetween in contact with the pair of electrodes. The step of texturing the face of at least one of the opposing electrodes may comprise grit blasting the face. The method may further comprise the step of applying the non-conductive material to at least one side wall adjacent to the face of at least one of the opposing electrodes. The face of the at least one opposing electrode may include a groove formed therein and the step of applying the non-conductive material forms a coating that has a difference in thickness on the face than in the grooves.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 16 is an example of a herringbone groove pattern for a vessel sealing system according to the present invention that cross-hatches with the herringbone pattern of FIG. 10; and.

FIG. 18 is a series of graphs of the surface topography of a vessel sealing system that has been coated according to the present invention.

DETAILED DESCRIPTION OF THE INVENTION

Figure 1:
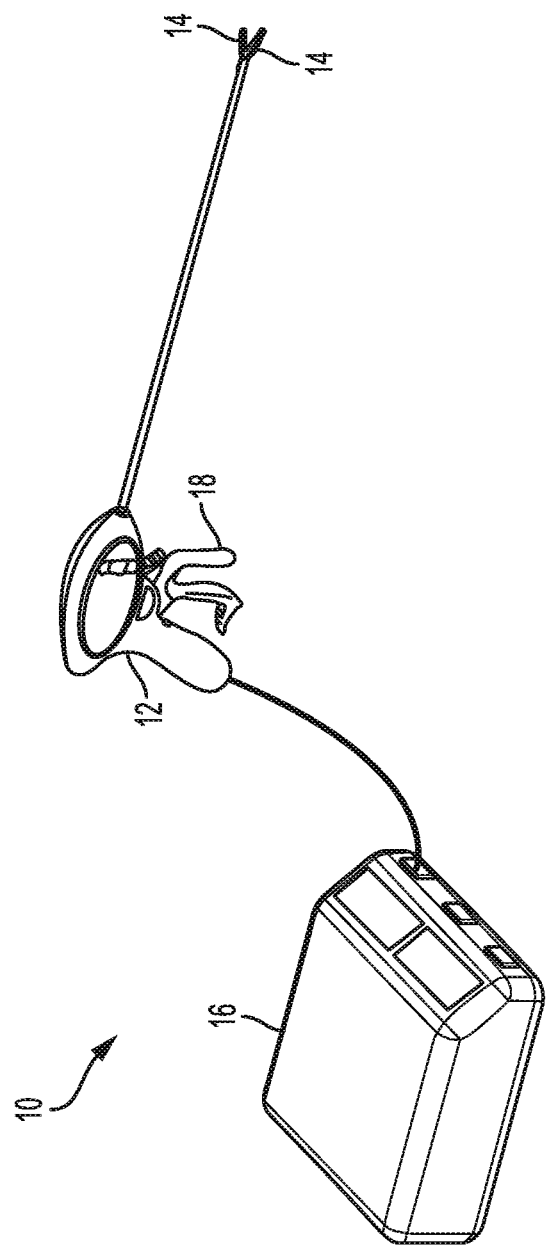
FIG. 1 is a perspective view of a vessel sealing system having coated electrodes according to the present invention.

Referring to the figures, wherein like numerals refer to like parts throughout, there is seen in FIG. 1 a vessel sealing system 10 comprising a vessel sealer 12 having a pair of conductive opposing electrodes 14 that are interconnected to an electrosurgical generator 16 that can supply RF energy to electrodes 14 for the desiccation of a blood vessel trapped between electrode 14. The dimensions of electrode 14 and the type of RF energy supplied to electrode 14 will produce desiccation of the blood vessel in a region of a particular width as determined by the thermal spread of the energy being supplied to the blood vessel. As is known in the art, electrode 14 may be held within non-conducting structures to form jaws that are hinged to allow electrode 14 to be open and closed in response to a user operating a handle 18 of sealer 12.

Figure 2:
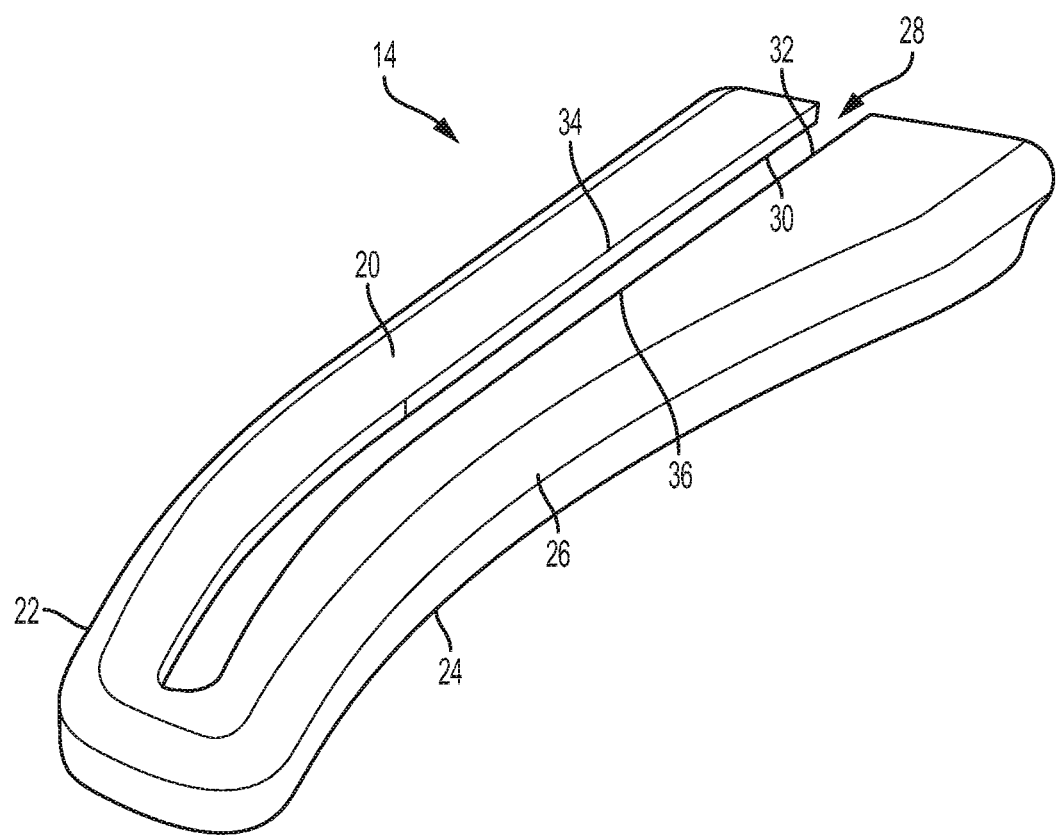
FIG. 2 is perspective view of one electrode of a vessel sealing system prior to coating according to the present invention.

As seen in FIG. 2, each electrode 14 has a generally planar face 20 for contacting the blood vessel that extends between two opposing sides 22 and 24 that define the width of face 20. The transition between face 20 and sides 22 and 24 is defined by a curved edge 26 having a predetermined radius. Electrode 14 further includes a track 28 defined by walls 30 and 32 extending from face 20. Walls 30 and 32 are spaced apart to allow a cutting instrument or knife (not shown) that may be disposed longitudinally in track 28 between both electrode 14 to sever a blood vessel within the region of thermal spread formed by the application of RF energy from the electrode 14 to the blood vessel. The intersection of walls 30 and 32 with face 20 defines a pair of opposing corners 34 and 36, shown in FIG. 2 as being substantially perpendicular.

Figure 3:
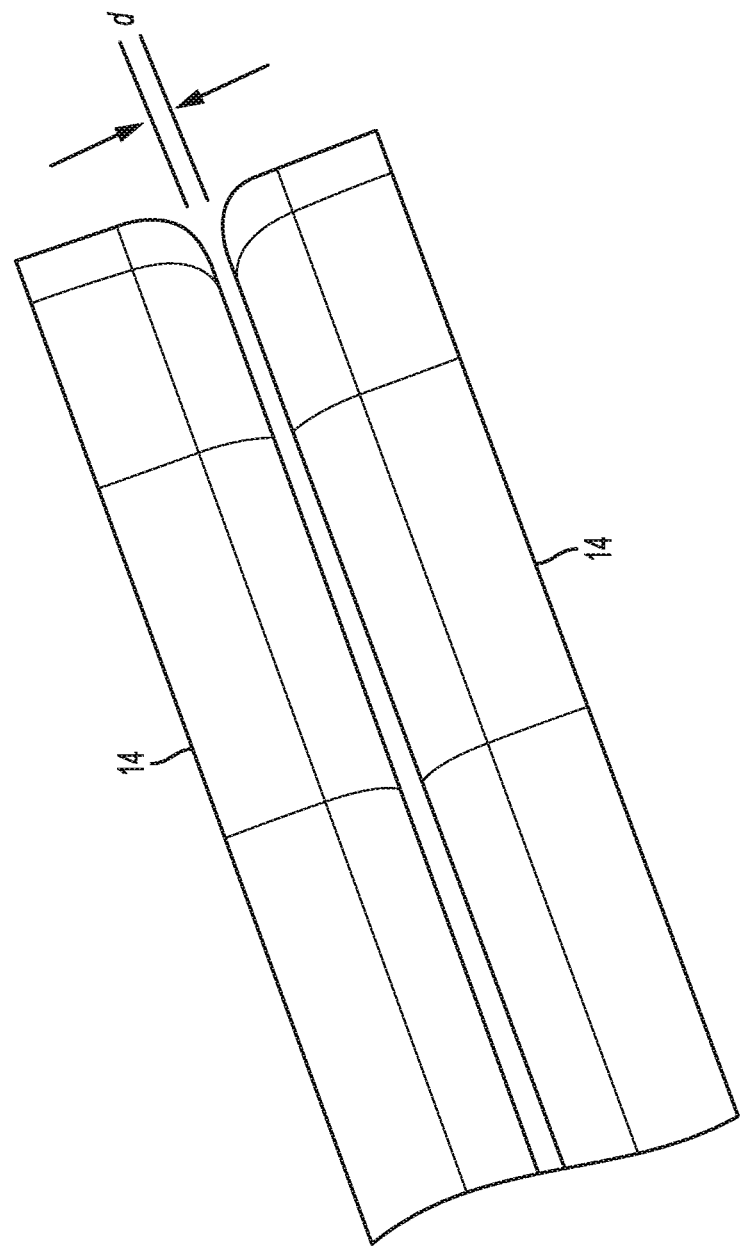
FIG. 3 is perspective view of the preferred gap between two electrodes of a vessel sealing system prior to coating according to the present invention.
Figure 4:
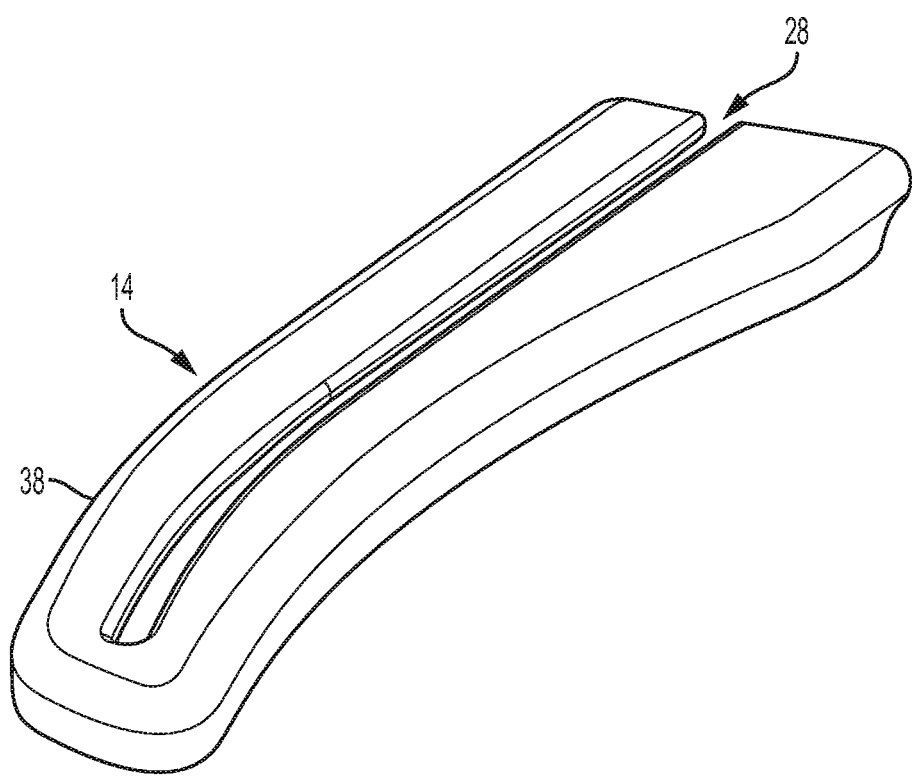
FIG. 4 is perspective view of one electrode of a vessel sealing system that has been coated according to the present invention.
Figure 5:
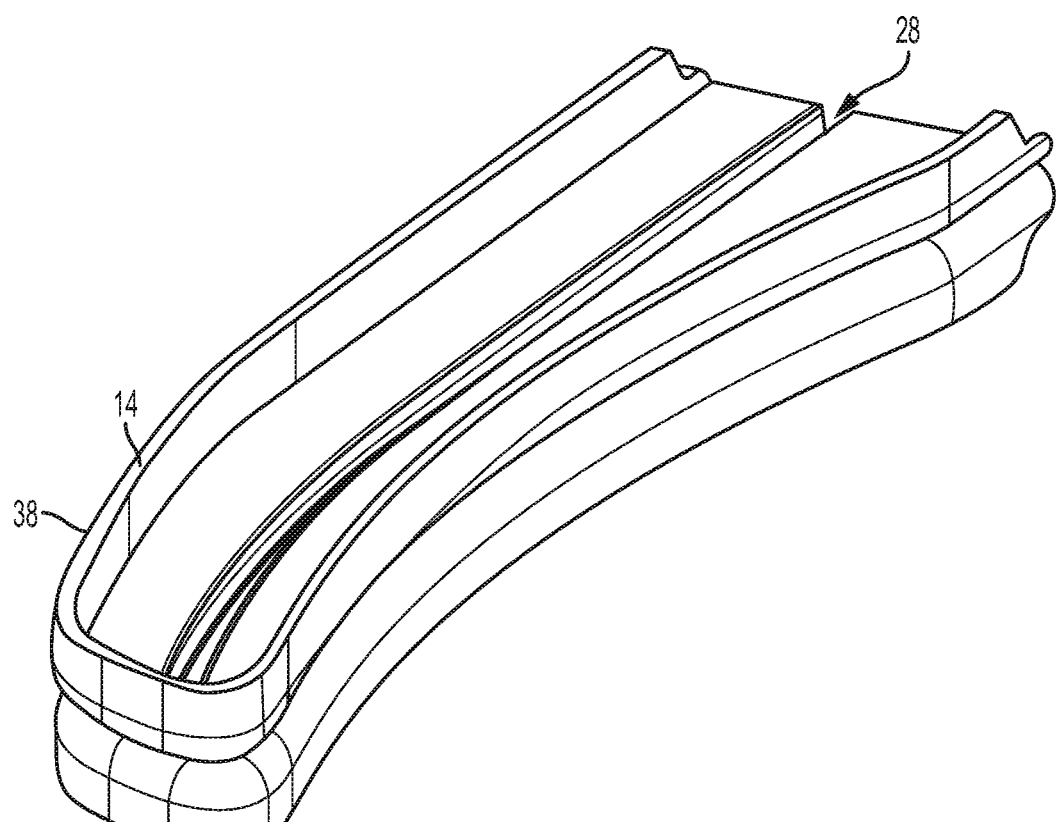
FIG. 5 is perspective view of two electrodes of a vessel sealing system that have been coated according to the present invention.
Figure 6:
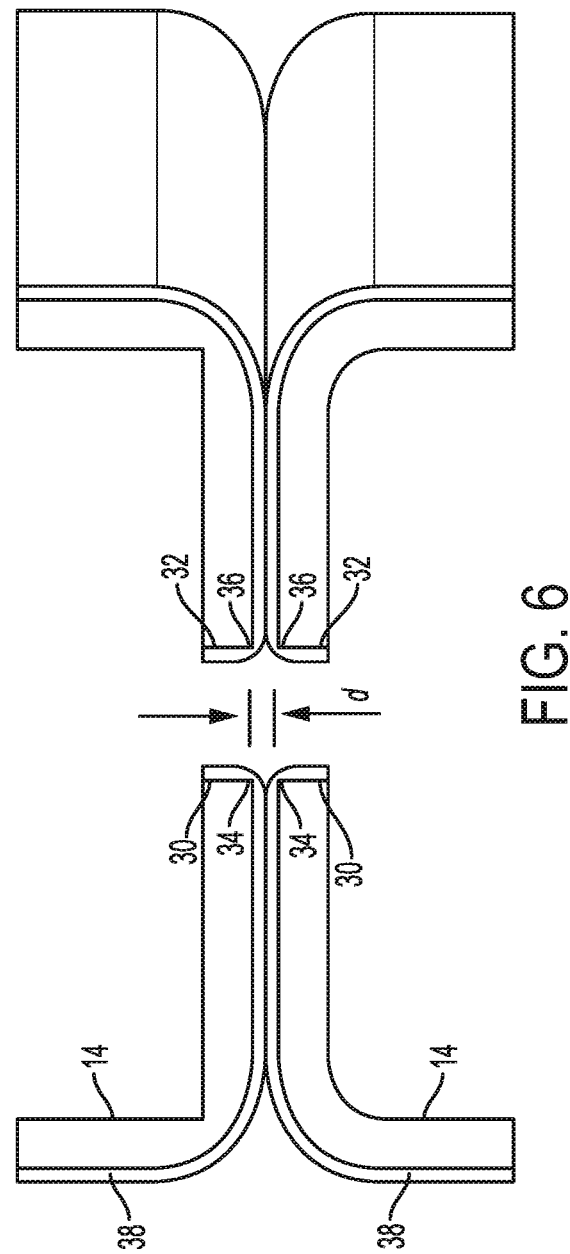
FIG. 6 is a cross-section of two electrodes of a vessel sealing system that have been coated according to the present invention.
Figure 7:
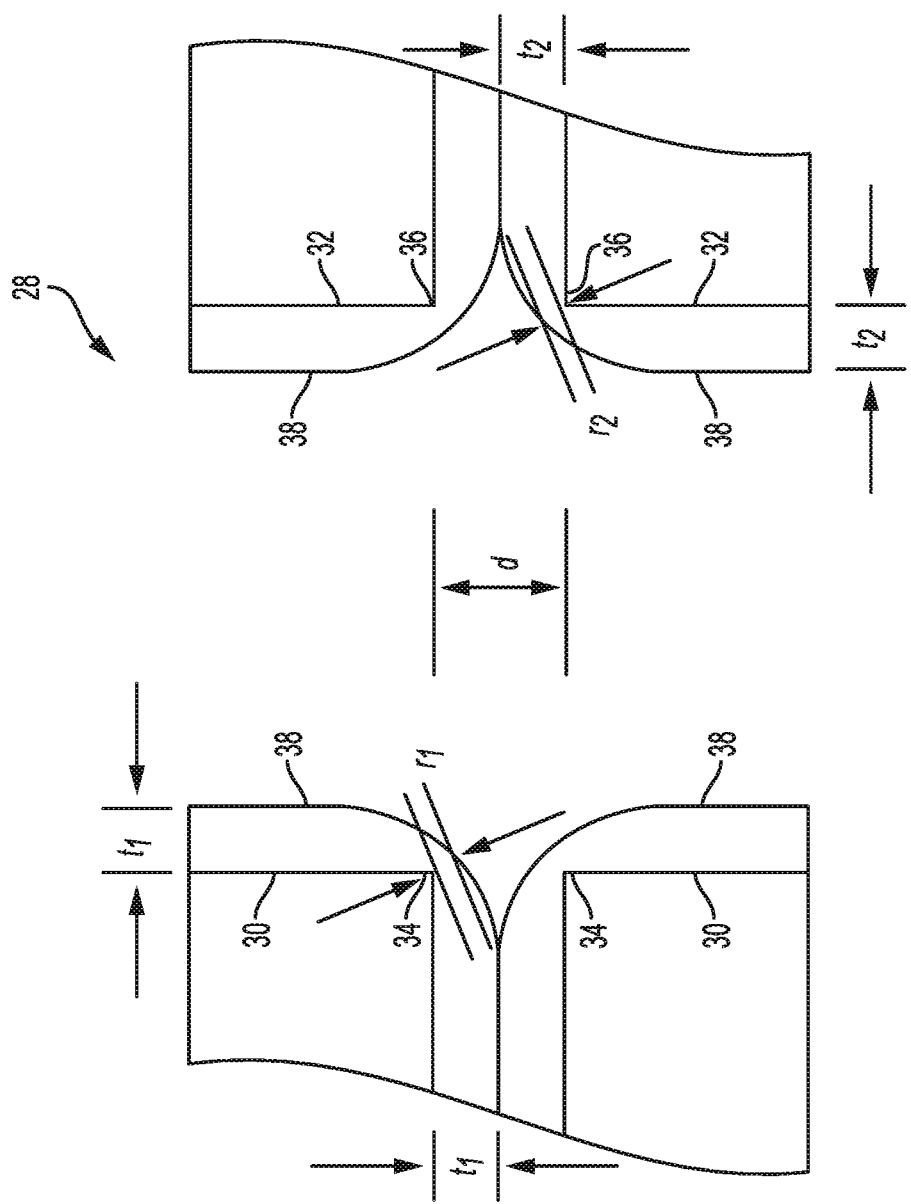
FIG. 7 is another cross-section of two electrodes of a vessel sealing system that have been coated according to the present invention.

Referring to FIG. 3, when electrode 14 are closed, they must remain separated by a specified distance d to prevent arcing or shorting when the RF energy is supplied by generator 16. As seen in FIG. 4, the required distance d may controlled via a coating 38 applied to at least one electrode 14 and, preferably, both electrode 14. As seen in FIG. 5, coating 38 may be applied to both electrode 14 so that the total thicknesses $t_1$ and $t_2$ of coating 38 produces distanced, such as that seen in FIGS. 6 and 7. While thickness $t_1$ and $t_2$ of coating 38 on electrode 14 is depicted in FIGS. 6 and 7 as generally the same, it should be recognized that coating of one electrode 14 may be thicker or thinner than the other electrode 14, providing that the sum of thicknesses $t_1$ and $t_2$ produce the desired distance d between electrode 14. For example, to obtain distance d of between 0.002 to 0.006 inches (0.0508 to 0.1524 millimeters), coating 38 may be applied to each electrode 14 to thickness of between 0.001 to 0.003 inches (0.0254 to 0.0762 millimeters).

Coating 38 may comprise a non-conductive material such as Teflon® (polytetrafluoroethylene/PTFE), ElectroBond (silicone epoxy), silicone rubber (polydimethylsiloxane), high temperature paints such as Thurmalox® 282 Stainless Steel paint, as well as ceramic coatings, glass based coatings, liquid crystal polymers, and high temperature engineering amorphous and semi-crystalline thermoplastics such as polysulfone (PSU), polyethersulfone (PES), polyphenylsulfone (PPSU), polytherimide (PEI), polyamide-imide (PAI), polyphthalamide (PPA), polyphenylene sulfide (PPS), and polyetheretherketone (PEEK). Coating 38 may be applied to electrode 14 via electrostatic spraying, fluid bed coating, plasma spray coating, and other conventional processes. Coating 38 may comprise a single layer applied at one or multiple layers applied by repeating the coating process. Coating 38 may additionally comprise multiple layers of different materials. It should be recognized that the non-conductive material selected for coating 38 and used to form distance d may provide additional benefits, such as a non-stick surface that reduces adhesion between electrode 14 and the blood vessel being desiccated.

Figure 8:
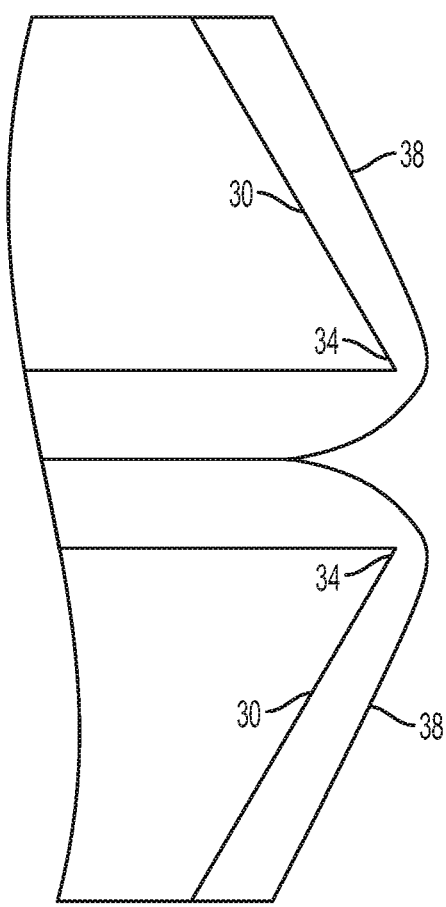
FIG. 8 is a cross-section of an electrode edge profile for controlling thinning of a coating according to the present invention.

Referring to FIG. 7, coating 38 does not have a uniform thickness across the entire electrode 14. Instead, upper and lower electrode 14 have corresponding regions $r_1$ and $r_2$ proximate to corners 34 and 36 where the thickness of coating 38 is reduced relative to the thicknesses of coating 38 proximately to face 20 and walls 30 and 32. The reduced thickness regions $r_1$ and $r_2$ may be controlled by the profile of walls 30 and 32 defining track 28. For example, as seen in FIG. 7, walls 30 and 32 connect to the respective faces 20 of electrode 14 at substantially right angles. Due to this angular profile, i.e., the edge formed by the intersection of walls 30 and 32 with face 20, coating 38 will be thinner when deposited on electrode 14 due to the surface tension of the molecules of coating 38 in combination with the composition of the substrate, i.e., face 20, the surrounding air, and the temperature of all components. Referring to FIG. 8, the geometry of the edge formed by the intersection of walls 30 and 32 with face 20 may be varied to control the dimension of reduced thickness regions $r_1$ and $r_2$, such as through the use of a more acute angle, a bevel, a small radius curve, or other geometric feature that reduces the thickness of coating 38 proximately to corners 34 and 36. Some radius may be allowable, but generally the sharper the angle the more thinning will occur. For example, a corner sharper than 90 degrees is likely to thin the coating even more, as seen in FIG. 8. Gravity may also be used thin the coating during application. If corners 34 and 36 are pointed upwardly during coating, gravity will augment the contact angle effect in thinning coating 38 at the edge.

While the dimensions of reduced thickness regions $r_1$ and $r_2$ may vary slightly based on the particular material chosen for coating 38, reduced thickness regions $r_1$ and $r_2$ should be thinner than thicknesses $t_1$ and $t_2$ of coating 38 positioned proximately to the remaining portions of electrode 14. For example, when coating 38 comprises silicone epoxy and PTFE and thicknesses $t_1$ and $t_2$ are 0.001 to 0.003 inches (0.0254 to 0.076 millimeters), reduced thickness regions $r_1$ and $r_2$ must be less than 0.001 inches (0.0254 millimeters) thick. For PTFE (600 V/mil dielectric strength) with an electrosurgical generator 16 that outputs 200 volts peak, $r_1$<200 V/600 V/mil=0.00033 inches (0.0084 millimeters). It should be recognized that these dimensions, as well as distance d, may vary from the exemplary dimensions are ultimately dependent on the intended use of system 10, such as the amount of RF energy being supplied and the effect system 10 is intended to have on the target tissues, and thus could be varied depending on the particular circumstances.

Figure 9A:
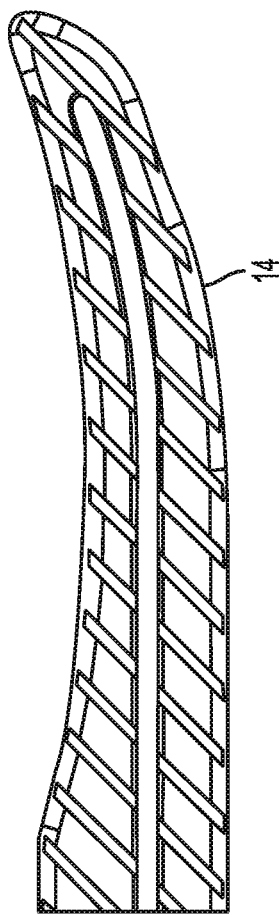
FIGS. 9A and 9B are exemplary patterns for increasing the number of current flow paths according to the present invention.
Figure 9B:
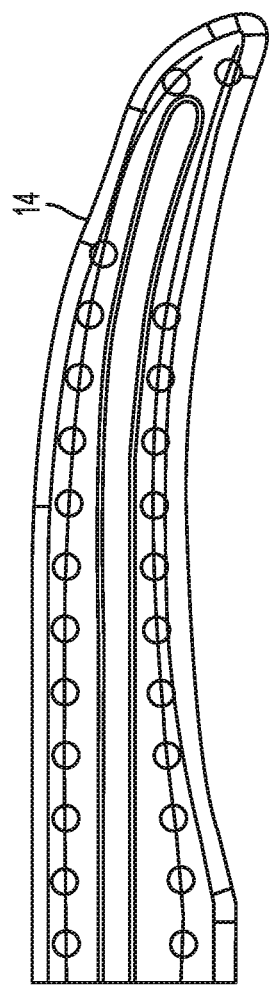

The reduced thickness regions $r_1$ and $r_2$ of the present invention allow for the flow of RF energy between electrode 14 despite the non-conductive material used of coating 38. As a result, RF energy is allowed to flow between electrode 14 at the locations where reduced thickness region $r_1$ of one electrode 14 is positioned opposite from reduced thickness region $r_2$ of the other electrode 14, i.e., desiccation occurs along track 28. This localization of RF energy transfer has the added benefit of more narrowly constraining the thermal spread in the target blood vessel and thus provide for improved control over the region where desiccation occurs in the blood vessel. Referring to FIGS. 9A and 9B, face 20 of electrode 14 may be patterned to increase the number of current flow paths by increasing the number of angular surfaces or edges formed by face 20 and thus increasing the number of locations where the thinning of coating occurs.

Figure 11:
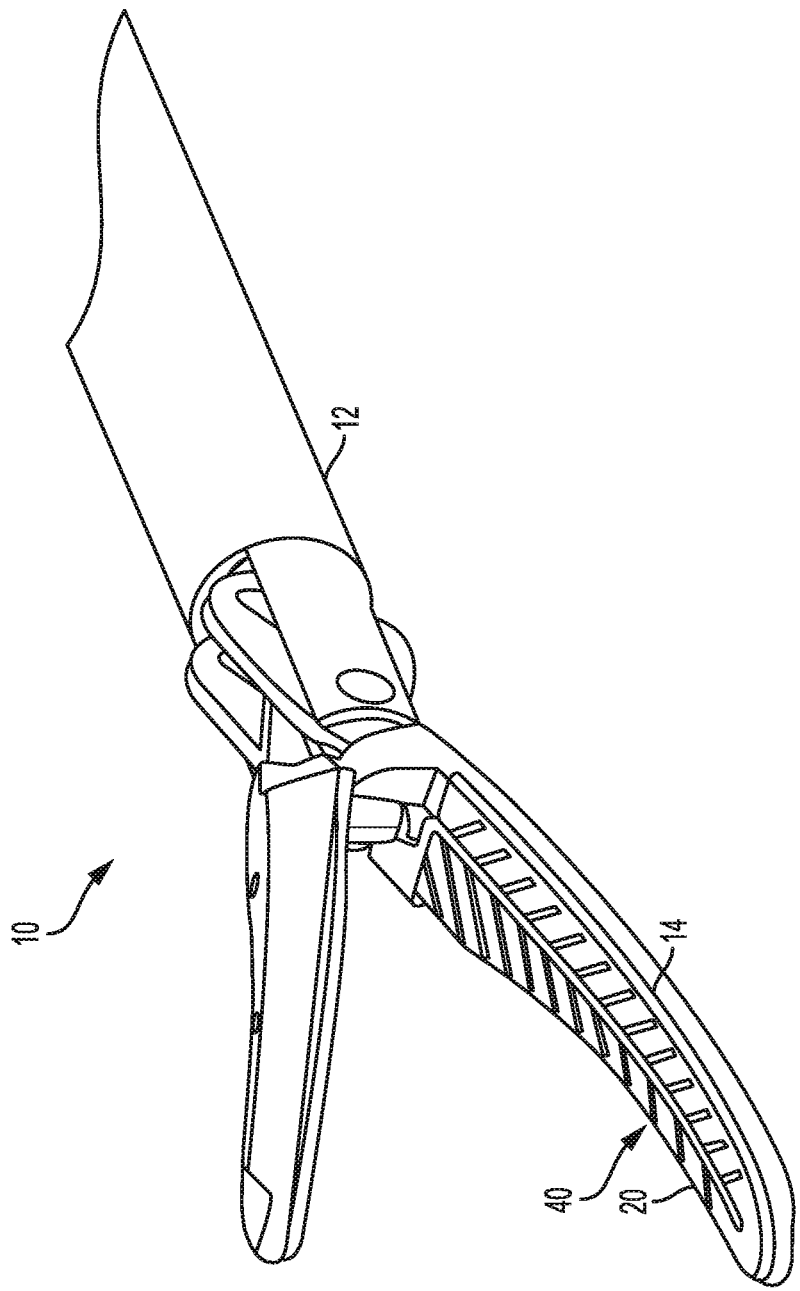
FIG. 11 is a perspective view of a vessel sealing system having uncoated electrodes according to the present invention.

Referring to FIG. 11, face 20 of electrode 14 may include a series of grooves 40 formed in a herringbone pattern to increase the number of locations having reduced thickness, i.e., reduced thickness regions $r_1$ and $r_2$ will form along the opposing edges 42 and 44 that define grooves 40 in addition to corners 34 and 36 of track 28. Face 20 of an opposing electrode 14 may be similarly patterned to correspond, either with a herringbone pattern that has grooves 40 that substantially align with the first electrode 14 or a herringbone pattern oriented in the opposite direction of grooves of first electrode 14 so that grooves 40 of one electrode 14 form a cross-hatching pattern with grooves of the other electrode 14 when they are positioned against each other.

In another aspect, the invention comprises a vessel sealing system 110 comprising a vessel sealer 112 having a pair of conductive electrodes 114 that are positioned in opposing jaws 116 and that may be interconnected to an electrosurgical generator (not shown) that selectively supplies RF energy to electrodes 114 for the desiccation of a blood vessel trapped between electrode 114. The dimensions of electrodes 114 and the type of RF energy supplied to electrodes 114 produce desiccation of the blood vessel in a region of a particular width may be determined by the thermal spread of the energy being supplied to the blood vessel. As is known in the art, electrodes 114 may be held within non-conducting jaws 116 that are hinged to allow two opposing electrodes 114 to be open and closed in response to a user operating a handle or trigger associated with sealer 112.

Each electrode 114 has a generally planar face 120 for contacting the blood vessel that extends between two opposing sides 122 and 124 that define the width of face 120. The transition between face 120 and sides 122 and 124 is defined by a curved edge 126 having a predetermined radius. Electrode 114 further includes a track 128 defined by walls 130 and 132 extending from face 120. Walls 130 and 132 are spaced apart to allow a cutting instrument or knife (not shown) that may be longitudinally extended and retraced along tracks 128 of both electrodes 114 to sever a blood vessel within the region of thermal spread formed by the application of RF energy from the electrode 114 to the blood vessel. The intersection of walls 130 and 132 with face 120 defines a pair of opposing corners 134 and 136, shown in FIG. 12 as being substantially perpendicular.

Figure 12:
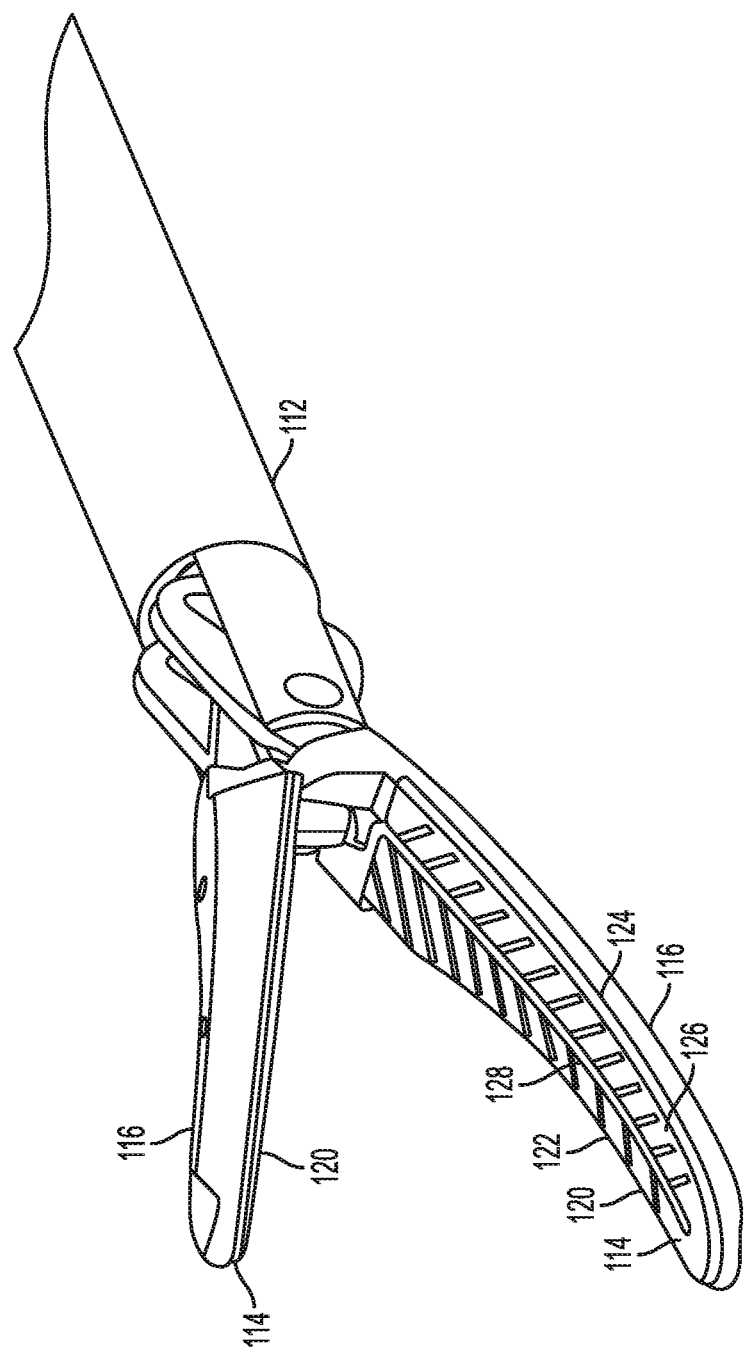
FIG. 12 is perspective view of one electrode of a vessel sealing system having coated electrodes according to the present invention.
Figure 13:
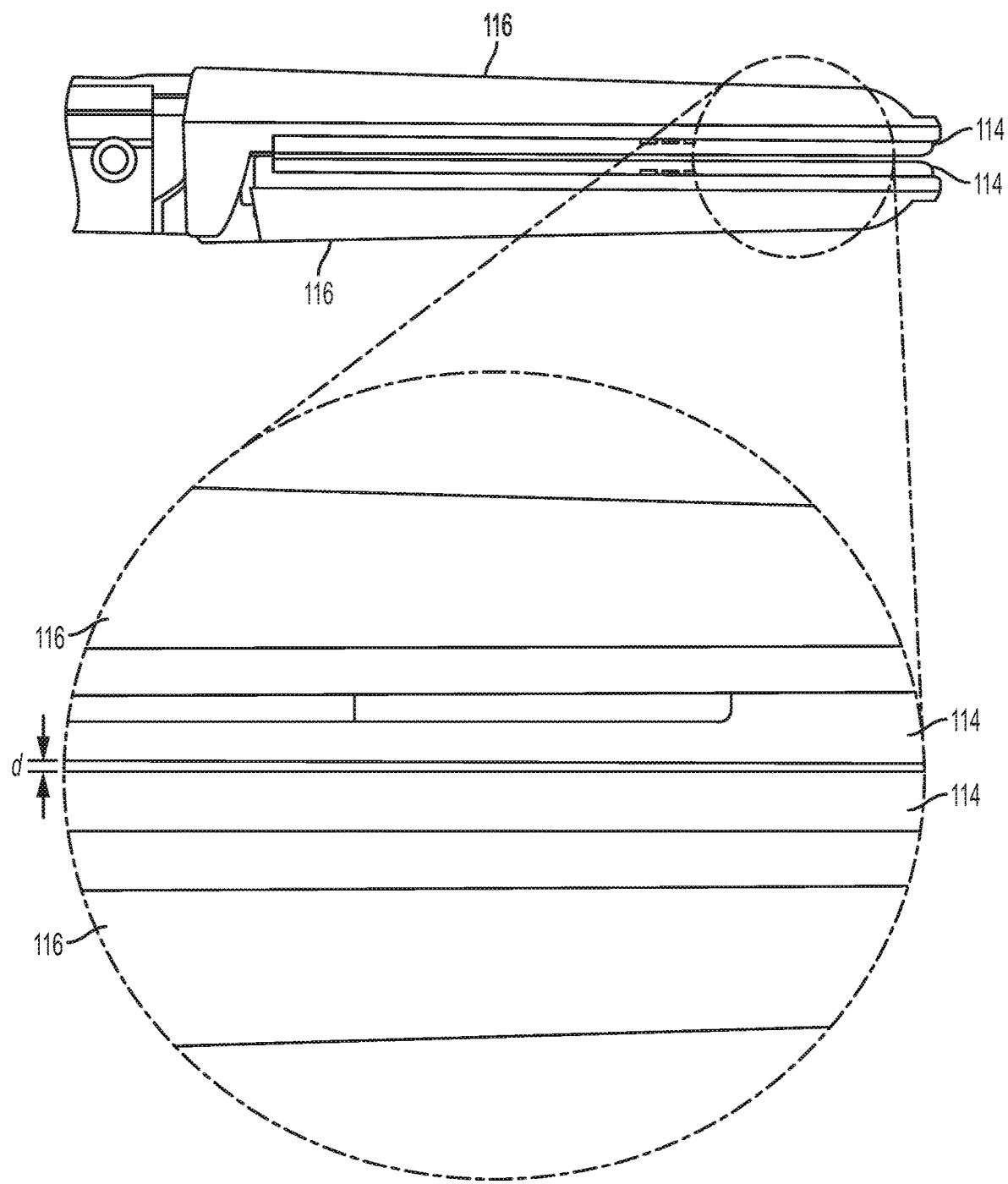
FIG. 13 is side view of a vessel sealing system having uncoated electrodes according to the present invention.
Figure 14:
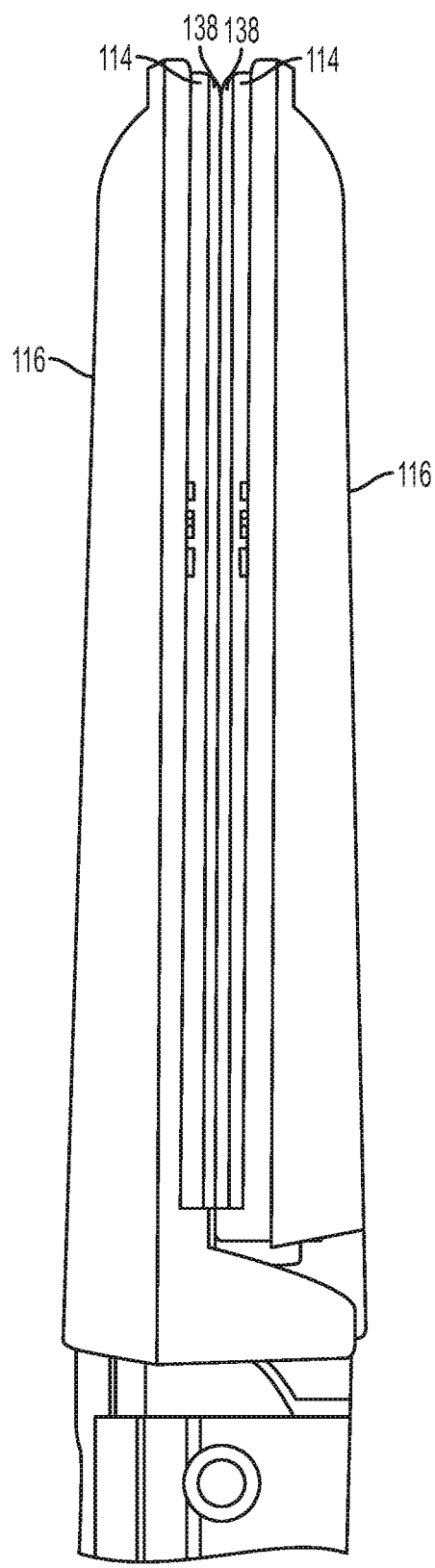
FIG. 14 is side view of a vessel sealing system having coated electrodes according to the present invention.

Referring to FIG. 12, when jaws 116 are closed, opposing electrodes 114 must remain separated by a specified distance d to prevent arcing or shorting when the RF energy is supplied by the external generator. As seen in FIG. 13, the required distance d may controlled via a non-uniform coating 138 applied to at least one of the opposing electrodes 14 and, preferably, both of the opposing electrodes 114, so that energy can flow between opposing electrodes 114 despite the present of non-uniform coating 138. Non-uniform coating 138 is applied to one or both electrodes 14 so that the total thicknesses $t_1$ and $t_2$ of coating 38 produces distance d. While thickness $t_1$ and $t_2$ of non-uniform coating 138 on each electrode 114, respectively, may the same, it should be recognized that non-uniform coating 138 of one electrode 14 may be thicker or thinner than non-uniform coating 138 of the other electrode 14, providing that the sum of thicknesses $t_1$ and $t_2$ produce the desired distance d between electrode 14. The thickness of non-uniform coating 138 on each of opposing electrodes 114 when applied to both of opposing electrodes 114, may be between 0.0005 inches (0.0127 millimeters) and 0.002 inches (0.0508 millimeters) with a preferred thickness of 0.001 inches (0.0254 millimeters).

Regardless of thickness, non-uniform coating 138 should be sufficient to prevent the flow of RF energy between opposing electrodes 114 during normal operating conditions if a vessel is not positioned therebetween. If a vessel is present, however, the non-uniformity of non-uniform coating 138 allows the vessel to contact enough of the uncoated or very thinly coated portions of electrodes 114 so that RF energy may flow between the electrodes 114 via the vessel despite the non-conductivity of the material used for coating 138. As a result, RF energy that flows between electrodes 114 will produce desiccation of any vessel trapped therebetween. Non-uniform coating 138 thus provides for a predetermined amount of RF energy to pass through an entrapped vessel for desiccation of the vessel tissue positioned between electrodes 114 when RF energy is applied while maintaining a sufficient gap distance between electrodes 114 to prevent arcing or shorting under normal conditions when no vessel is present. While non-uniform coating 138 can theoretically allow energy flow under extreme conditions, e.g., enough RF energy to ionize the air so that it becomes conductive, the purpose of non-uniform coating 138 is to prevent flow during the operating conditions that system 10 can actually experience when a vessel is not positioned between the electrodes and to allow energy to flow when a vessel is clamped between the electrodes under reasonable operating conditions available to conventional RF generators and in amounts that are useful for electrosurgical operations. For example, non-uniform coating 138 may be applied in a manner such that the pair of opposing electrodes have approximately 400 ohm of starting resistance in a constant power mode of 20-100 Watts with a voltage of 80-160 Vrms when positioned around and in contact with an exemplary vessel. Thus, one embodiment may have 400 ohm of starting resistance in a constant power mode of 25 Watts with a voltage of 100 volts when positioned around and in contact with a vessel. The appropriate resistance may be accomplished by using non-uniform coating 138 to produce a gap of more than 0.001 inches between the electrodes. Thus, non-uniform coating 138 may have a total thickness of 0.0008 inches±0.0002 inches, so when applied to both electrodes 114, the total thickness and thus gap distance will be slightly below 0.0020 inches but still effective in preventing shorting or arcing when a vessel is not positioned between electrodes 114. It should be recognized that power levels may need to vary with the size of electrodes 114 and with different overall thicknesses of non-uniform coating 138. For example, an acceptable non-uniform coating 138 can vary in starting impedance from as high as around 600-800 ohm to as low as 150 or 200 ohm depending on the thickness of non-uniform coating 138.

Non-uniform coating 138 may comprise a non-conductive material such as Teflon® (polytetrafluoroethylene/PTFE), ElectroBond (silicone epoxy), silicone rubber (polydimethylsiloxane), high temperature paints such as Thurmalox® 282 Stainless Steel paint, as well as ceramic coatings, glass based coatings, liquid crystal polymers, and high temperature engineering amorphous and semi-crystalline thermoplastics such as polysulfone (PSU), polyethersulfone (PES), polyphenylsulfone (PPSU), polytherimide (PEI), polyamide-imide (PAI), polyphthalamide (PPA), polyphenylene sulfide (PPS), and polyetheretherketone (PEEK). It should be recognized that the non-conductive material selected for coating 138 and used to form distance d may provide additional benefits, such as a non-stick surface that reduces adhesion between electrode 114 and the blood vessel being desiccated.

Figure 15:
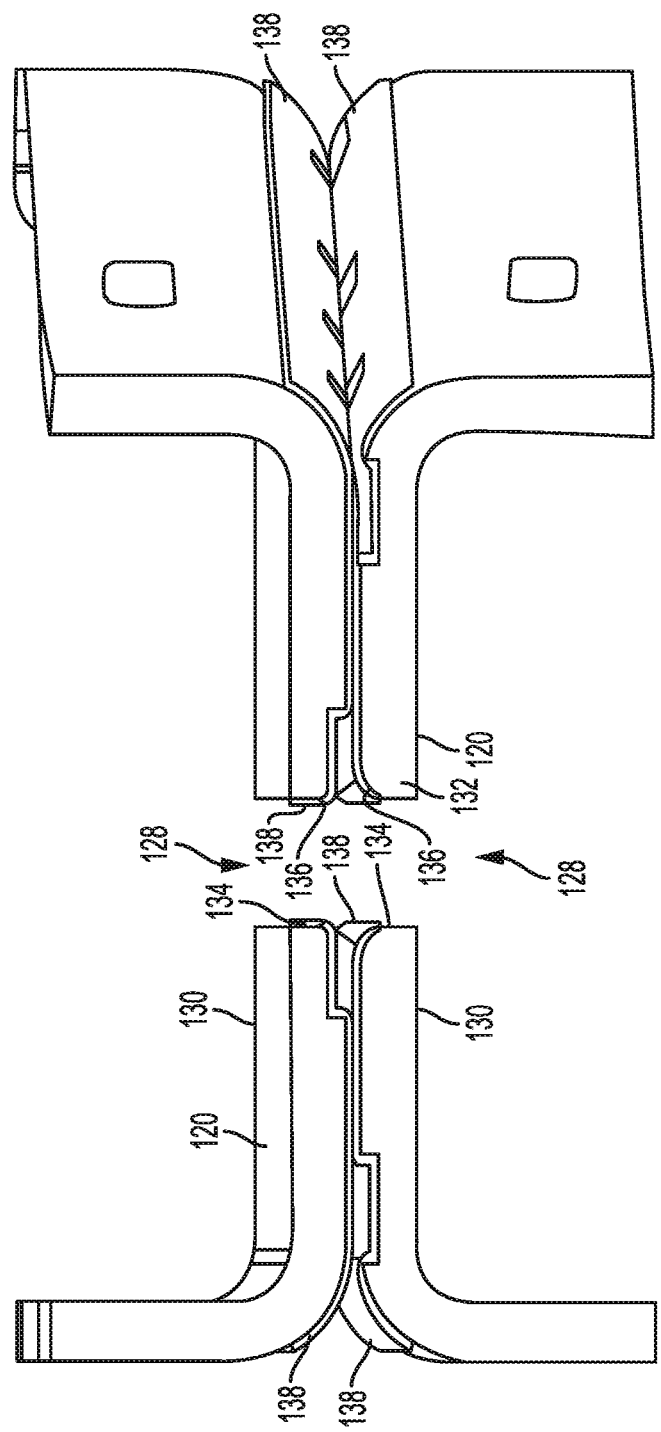
FIG. 15 is cross-sectional view of two electrodes of a vessel sealing system that have been coated according to the present invention.

Referring to FIG. 15, non-uniform coating 138 is provided across each electrode 114, beginning with a portion of the two opposing sides 122 and 124 that define the width of face 120 and extending over curved edge 126 at the transition between sides 122 and 124 and face 120. Coating 138 extends across the planar surface of face 120, the pair of opposing corners 134 and 136, and walls 130 and 132 that define track 128.

Figure 10:
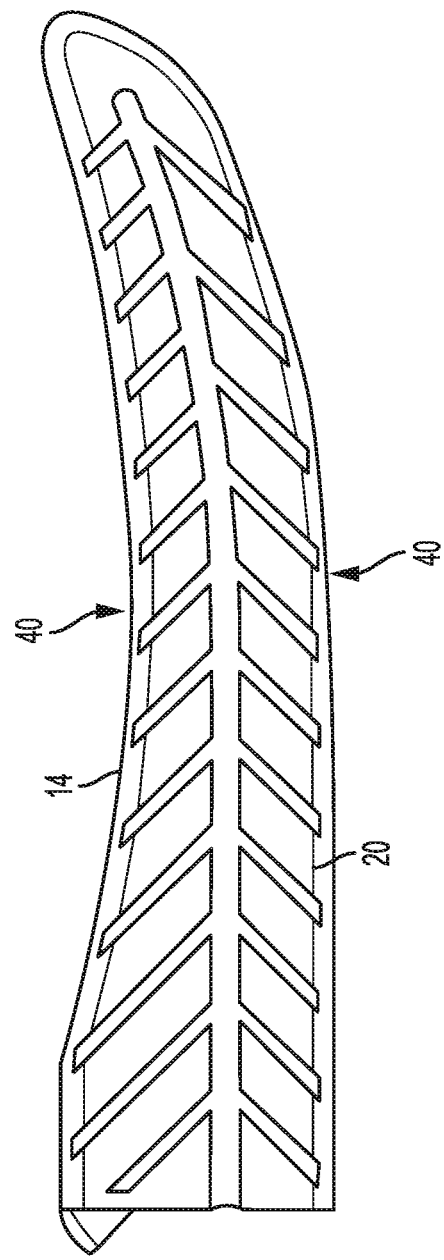
FIG. 10 is an example of a herringbone groove pattern for a vessel sealing system according to the present invention.
Figure 16:
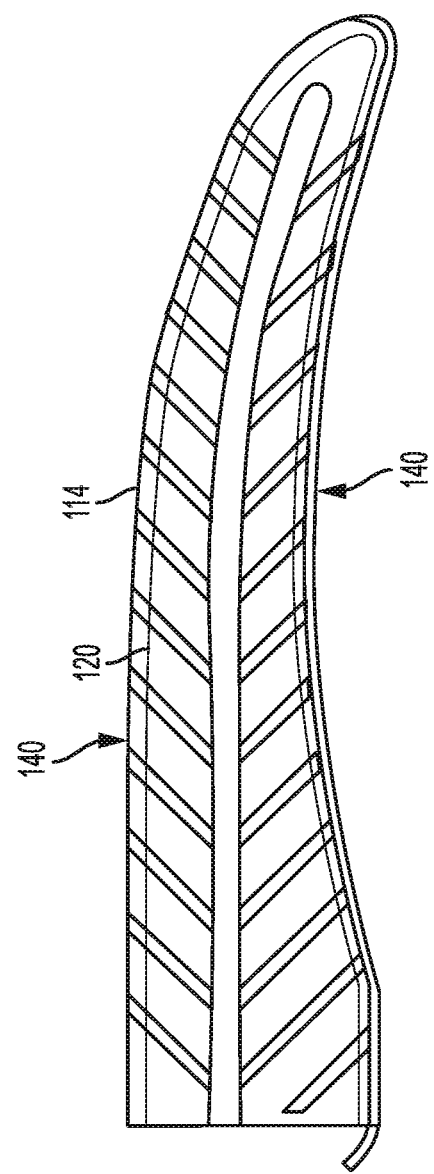
Figure 17:
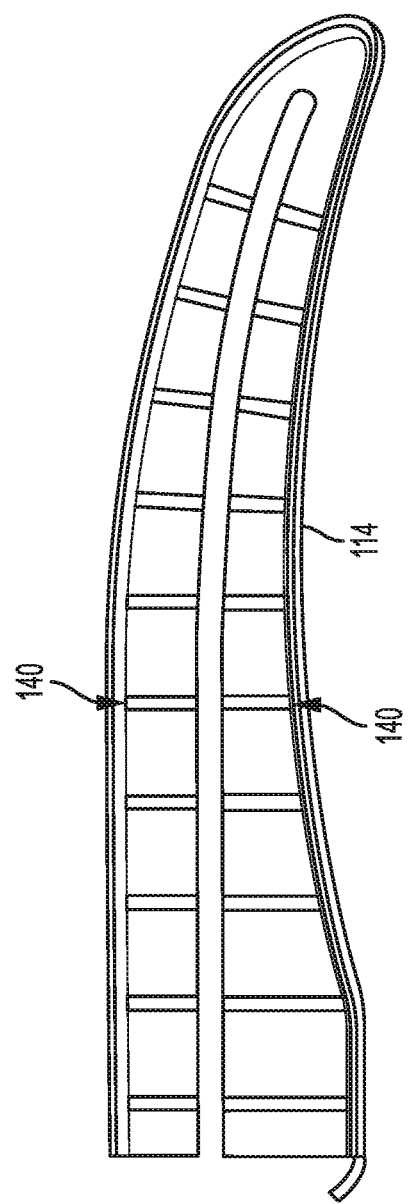
FIG. 17 is an example of a transverse groove pattern for a vessel sealing system according to the present invention.

As further seen in FIG. 16, face 120 may include grooves 140 or other topological features that are also covered with coating 138. For example, as seen in FIG. 16, face 120 includes a plurality of grooves 140 arranged in a herringbone pattern. Face 120 of an opposing electrode 114 may be similarly patterned to correspond, either with a herringbone pattern that has grooves 140 that substantially align with the first electrode 114 or a herringbone pattern oriented in the opposite direction of grooves of first electrode 114 so that grooves 140 of one electrode 114, such as that seen in FIG. 10, to form a cross-hatching pattern with grooves 40 of the other electrode 114 when electrodes 114 are positioned against each other. Referring to FIG. 17, grooves 140 may also extend transversely across electrodes 114 so that grooves 140 are perpendicular to the longitudinal axis of face 120.

Non-uniform coating 138 is created by performing a thermal burn off and then grit blasting of the uncoated electrodes 114 to form a roughened topological surface on electrodes 114. Electrodes 114 are then masked and coated with the coating material to form non-uniform coating 138. The coated electrodes 114 are thermally cured in an oven and inspected.

As seen in FIG. 18, the face of an electrode 114 that has been prepared and coated non-uniformly with a non-conductive material according to the present invention so that the coated electrode 114 has non-uniform topological surface with regions of relatively thickly applied coating interspersed with regions that are not coated or very thinly coated. It should be recognized that the amount of non-uniformity may be varied to adjust and control the ability of the electrode 114 to conduct RF energy therebetween when a vessel is in contact with the non-uniform surface such that portions of the vessel come into contact with the uncoated or thinly coated regions. Thus, the more thickly coated regions serve to provide spacing between electrodes 114 to prevent arcing or shorting when a vessel is not present, and the very thinly or uncoated regions allow for conductivity when a vessel comes into contact with those regions and completes the circuit. The amount of non-uniformity may be controlled by varying the amount of grit blasting, the amount and thickness of non-conductive material applied to the grit-blasted face, and the particular non-conductive material used. In the example of FIG. 18, the surface of face 120 has a total profile that varies between −5.8 micrometers and 6.2 micrometers from the centerline average, and a roughness profile that varies between −6.5 micrometers and 6.5 micrometers from the centerline average. In an example, the percentage of electrodes 114 that are exposed by non-uniform application of the coating is around 1.5% of the non-uniformly coated area.

In a first aspect, the invention is an electrode for a vessel sealing device, comprising a face extending along a planar surface, a pair of opposing walls extending from the face at a pair of opposing corners to define a knife track between the pair of opposing walls, and a non-conductive coating covering at least a portion of the face, the pair of opposing walls, and the opposing corners.

In a second aspect, the coating has a first thickness proximately to the face and the opposing walls and a second thickness that is less than the first thickness proximately to the pair of opposing corners.

In a third aspect, the second thickness is less than the first thickness.

In a fourth aspect, the first thickness is between 0.001 to 0.006 inches (0.025 to 0.152 millimeters).

In a fifth aspect, the first thickness is between 0.001 and 0.003 inches (0.025 to 0.0762 millimeters).

In a sixth aspect, the non-conductive coating is selected from the group consisting of polytetrafluoroethylene (PTFE), silicone epoxy, silicone rubber, polysulfone (PSU), polyethersulfone (PES), polyphenylsulfone (PPSU), polytherimide (PEI), polyamide-imide (PAI), polyphthalamide (PPA), polyphenylene sulfide (PPS), and polyetheretherketone (PEEK).

In a seventh aspect, the invention may be a vessel sealing device, comprising a pair of jaws, wherein each jaw has an electrode with a face extending along a planar surface and a pair of opposing walls extending from the face at a pair of opposing corners to define a knife track between the pair of opposing walls, and a non-conductive coating covering at a minimum the face, the pair of opposing walls, and the opposing corners of each electrode.

In an eighth aspect, the coating has a first thickness proximately to the face and the opposing walls and a second thickness that is less than the first thickness proximately to the pair of opposing corners.

In a ninth aspect, the second thickness is less than the first thickness.

In a tenth aspect, the first thickness is between 0.001 and 0.003 inches (0.025 to 0.0762 millimeters).

In an eleventh aspect, the non-conductive coating is selected from the group consisting of is selected from the group consisting of polytetrafluoroethylene (PTFE), silicone epoxy, silicone rubber, polysulfone (PSU), polyethersulfone (PES), polyphenylsulfone (PPSU), polytherimide (PEI), polyamide-imide (PAI), polyphthalamide (PPA), polyphenylene sulfide (PPS), and polyetheretherketone (PEEK).

What is claimed is:

1. A vessel sealing device, comprising:
   a pair of electrodes formed from a conductive material and each having one of a pair of planar surfaces defining a face that are movable between open and closed positions to capture a vessel therebetween; and a coating on the pair of planar surfaces, wherein the coating is formed from a non-conductive material and has a non-uniform topological surface characterized by a plurality of thicker regions interspersed with a plurality of thinner regions relative to each other such that any radiofrequency energy supplied by a radiofrequency generator in a constant power mode between 20 and 100 Watts with a voltage of between 80 and 160 root mean square voltage will pass between the pair of electrodes if the vessel is captured between the planar surfaces but will not pass if the vessel is absent;

wherein the coating on the pair of planar surfaces of the pair of electrodes has a total profile that varies between −5.8 micrometers and 6.2 micrometers from a centerline average and a roughness profile that varies between −6.5 micrometers and 6.5 micrometers from a centerline average.

2. The vessel sealing device of claim 1, further comprising a series of grooves formed in the face of each of the electrodes.

3. The vessel sealing device of claim 2, wherein the series of grooves of the face of each of the electrodes extend transversely to the longitudinal axis of the face of each of the electrodes.

4. The vessel sealing device of claim 3, wherein the series of grooves of the face of each of the electrodes are oriented in a herringbone pattern.

5. The vessel sealing device of claim 4, wherein the face of each of the electrodes extends from two opposing side walls to an inner track.

6. The vessel sealing device of claim 5, wherein the coating extends across at least a portion of the side walls.

7. A method of making a vessel sealing device having a pair of electrodes, comprising the steps of:

texturing a pair of planar surfaces, each of which is formed from a conductive material and forms a face of one of the electrodes; and applying a non-conductive material to the textured face to form a coating that has a non-uniform topological surface characterized by a plurality of thicker regions interspersed with a plurality of thinner regions relative to each other, such that any radiofrequency energy supplied by a radiofrequency generator in a constant power mode between 20 and 100 Watts with a voltage of between 80 and 160 root mean square will pass between the pair of electrodes if a vessel is captured between the planar surfaces but not if the vessel is absent; wherein the coating on each of the pair of electrodes has a total profile that varies between −5.8 micrometers and 6.2 micrometers from a centerline average and a roughness profile that varies between −6.5 micrometers and 6.5 micrometers from a centerline average.

8. The method of claim 7, wherein the step of texturing the pair of planar surfaces of the electrodes comprises grit blasting each face of the electrodes.

* * * * *